(12) United States Patent
Cerni et al.

(10) Patent No.: US 6,903,818 B2
(45) Date of Patent: Jun. 7, 2005

(54) LOW NOISE INTRACAVITY LASER PARTICLE COUNTER

(75) Inventors: Todd A. Cerni, Mead, CO (US); Dwight A. Sehler, Longmont, CO (US); Mark A. Lilly, Lafayette, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 325 days.

(21) Appl. No.: 10/282,169

(22) Filed: Oct. 28, 2002

(65) Prior Publication Data

US 2004/0080747 A1 Apr. 29, 2004

(51) Int. Cl.[7] .......................... G01N 21/00; G01N 21/47
(52) U.S. Cl. ...................... 356/338; 356/339; 356/436; 250/341.8
(58) Field of Search ............................... 356/336–343, 356/436, 411; 250/574–575, 222.2, 423 R, 339.13, 341.8

(56) References Cited

U.S. PATENT DOCUMENTS

| | | | | |
|---|---|---|---|---|
| 3,700,333 A | * | 10/1972 | Charlson et al. | 356/339 |
| 3,983,743 A | * | 10/1976 | Olin et al. | 73/28.06 |
| 4,992,190 A | * | 2/1991 | Shtarkman | 252/62.52 |
| 5,872,361 A | * | 2/1999 | Paoli et al. | 250/341.8 |
| 5,889,589 A | | 3/1999 | Sandberg | |
| 5,946,093 A | * | 8/1999 | DeFreez et al. | 356/339 |
| 6,091,494 A | * | 7/2000 | Kreikebaum | 356/336 |
| 6,137,572 A | * | 10/2000 | DeFreez et al. | 356/336 |
| 6,275,288 B1 | * | 8/2001 | Atkinson et al. | 356/246 |
| 6,404,494 B1 | * | 6/2002 | Masonis et al. | 356/338 |
| 6,414,754 B1 | * | 7/2002 | Johnson | 356/338 |
| 6,710,878 B1 | * | 3/2004 | Dean et al. | 356/436 |

* cited by examiner

*Primary Examiner*—Gregory J. Toatley, Jr.
*Assistant Examiner*—Sang H. Nguyen
(74) *Attorney, Agent, or Firm*—Patton Boggs LLP

(57) ABSTRACT

An optical particle counter has a gain-apertured laser cavity producing laser light, an inlet jet providing fluid flow into a particle detecting region within the laser cavity, the inlet jet having an inlet jet orifice; a detection optics assembly located to collect light scattered from particles with the detecting region for producing an output signal indicative of the particles; and an optical barrier complex located to reduce noise as compared to the gain-apertured system without the optical barrier complex for fluid flow rates greater than or equal to about 0.1 cubic feet per minute. The optical barrier complex inhibits laser light from illuminating turbulent eddy currents originating on the interior walls of the inlet jet. The optical barrier complex includes one or more physical apertures, one or more optical stops, or both which are located to prevent laser light from illuminating the eddy currents.

28 Claims, 6 Drawing Sheets

Figure 1:
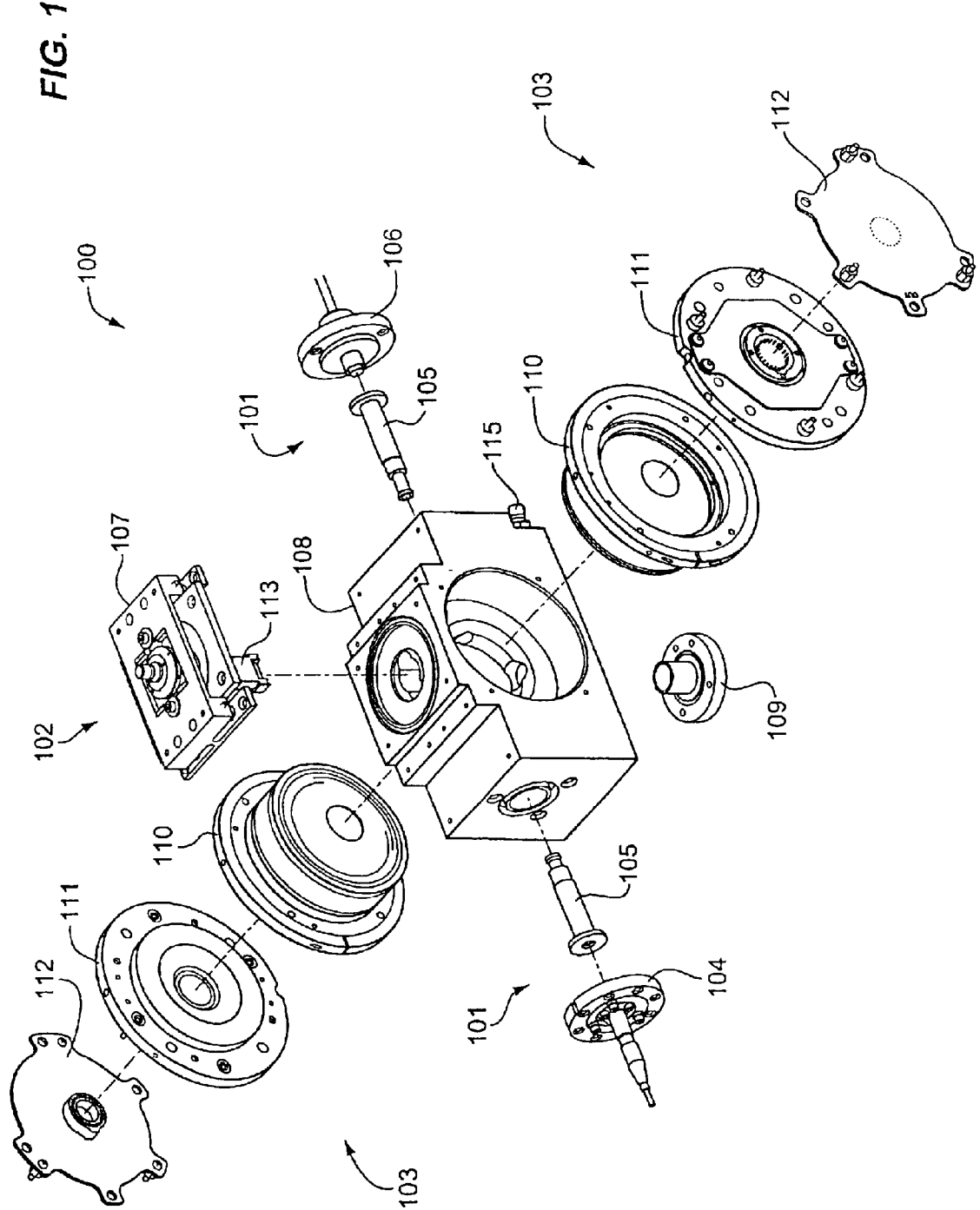

FIG. 6A
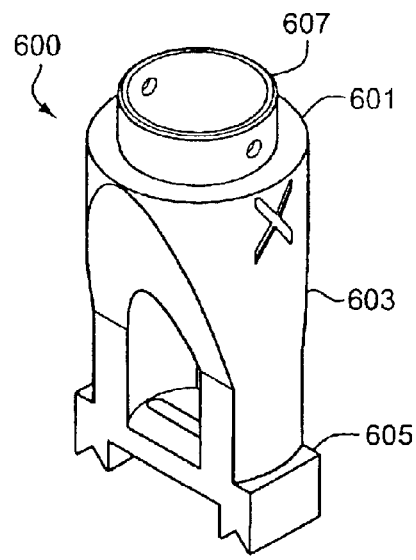
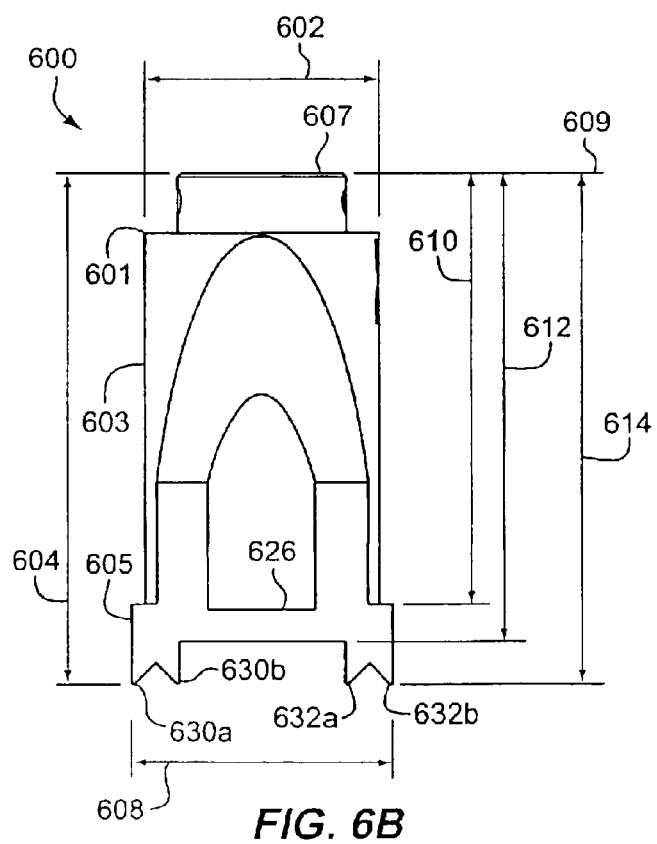
FIG. 6B
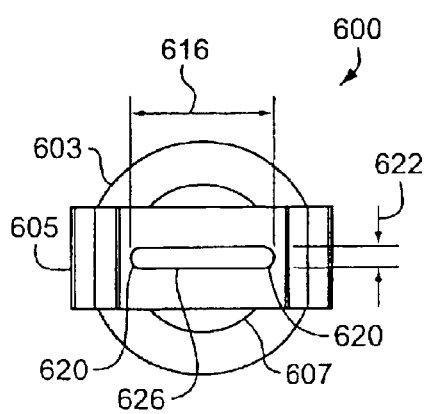
FIG. 6C

LOW NOISE INTRACAVITY LASER PARTICLE COUNTER

BACKGROUND OF THE INVENTION

1. Field of the Invention

The present invention relates in general to systems which utilize light scattering principles to detect and count undesirable particles in fluids, referred to in the art as light scattering particle counters, and more particularly to high power, low noise intracavity laser particle counters.

2. Statement of the Problem

The history of the semiconductor industry has shown a consistent path of steadily decreasing line widths. The semiconductor industry roadmap for the future shows this trend continuing unabated. Smaller semiconductor line widths mean smaller critical defect sizes, which in turn require detection of smaller particles, for effective contamination monitoring of clean room air. Accordingly, the semiconductor roadmap continually pushes researchers to develop ever more sensitive OPCs (optical particle counters), to measure ever smaller particle sizes. To achieve a statistically valid sample in a reasonable amount of time, when operating in a very clean environment, high performance OPCs should also have high sample rates (volume of air sampled per unit time).

An existing particle detection system is described in U.S. Pat. No. 5,889,589 issued Mar. 30, 1999 to Jon C. Sandberg (the '589 patent), which patent is hereby incorporated herein by reference. The OPC of the '589 patent measures scattered laser radiation from particles which pass through a sample volume. The magnitude of the scattered laser radiation is proportional to particle size, and each particle generates a single optical pulse. This allows the particle counter to detect particles which pass through the sample volume. For particles much smaller than the laser wavelength (the "Rayleigh range"), the magnitude of scattered laser radiation is proportional to the sixth power of the particle diameter. Hence, it quickly becomes very difficult to measure smaller and smaller particles.

To take advantage of the high intracavity power of the solid-state laser, the sample air is directed through the laser's active cavity by an inlet jet, placed proximate to the laser beam. Sample air is drawn through the sample volume by applying a vacuum source to the outlet jet.

The laser medium is optically pumped by an optical pump source whose output is generally coupled through a focusing lens system. The laser medium element can be one of a family of crystals such as Nd:YAG, Nd:YLF, Nd:YALO, Nd:YVO4. By using a lens to focus the diode laser pump radiation to a small waist within the solid-state laser crystal, aperture control is obtained through gain-aperturing. This design leads to a single transverse mode and high intracavity power.

The '589 patent identifies several benefits of its gain-aperturing system over the prior art including enabling operation with weak dependence on the shape, size, and alignment of the pumped volume, reducing flow induced laser noise, and allowing high power operation. See the '589 patent, column 6, lines 11–27. The '589 patent also identifies problems associated with combining physical aperturing with, gain aperturing. After describing an embodiment in which an aperture having a diameter of about one millimeter is added to a gain-apertured system, the '589 patent asserts that "the presence of the physical, aperture adversely affects intracavity power and relative noise as flow rate is increased." See the '589 patent, column 7, lines 6–8. Accordingly, the '589 patent specifically teaches away from combining physical aperturing with gain aperturing.

To accurately detect very small particles, such as 0.065 micrometer ($\mu$m) or still smaller particles, in a fluid flowing at a rate greater than or equal to 1.0 Cubic Feet per Minute (CFM), at an efficiency level of 30% or higher, it is highly desirable to provide a laser system having low noise as well as high power operation. The particle counter of the '589 patent experiences higher than desired noise levels, characterized by bursts of relatively large amplitude noise. Detector thresholds generally have to be set high enough to reject the worst case noise, so as to reject false counts. However, these elevated thresholds generally inhibited the effective detection of very small particles with a reasonable counting efficiency, at fluid flow rates greater than or equal to 1.0 CFM.

Accordingly, there is a need in the art to preserve high power laser operation while reducing the noise level of such lasers so as to permit effective detection of small particles at a desired counting efficiency at fluid flow rates equal to or less than 1.0 CFM.

SUMMARY OF THE INVENTION

The present invention advances the art and helps to overcome the aforementioned problems by providing a system which combines high power operation with effective noise reduction to enable efficient counting of very small particles in an OPC. The invention provides an optical particle counter that includes both gain aperturing and an optical barrier that physically intercepts portions of the laser beam that contribute to noise. In particular, it has been found that turbulent eddies breaking off the fluid inlet jet can scatter light which, contributes to stray light that can enter the light detector. It has been found that an optical barrier, such as a laser beam aperture or an optical stop, effectively reduces this stray light.

One embodiment of the invention provides an intracavity particle counter which employs an optical barrier complex to inhibit diffusion of laser light toward turbulent and/or eddy current flow. The flow concerned is generally in proximity to an inlet jet orifice and generally outside a particle detection region of the intracavity particle counter.

The invention provides a method for intracavity laser detection of optically detecting single particles, the method comprising: providing a solid state laser cavity having laser light; gain-aperturing the laser cavity with an optical pump; providing fluid flow including a particle at a detection region within the gain-apertured laser cavity illuminated by the laser light; collecting light scattered by the particle and producing an output signal indicative of the particle; and locating an optical barrier complex to reduce noise in the output signal at flow rates of the fluid flow greater than or equal to about 0.1 cubic feet per minute. Preferably, the particle has a size of 0.1 micron or less. Preferably, the locating comprises locating the optical barrier complex to reduce flow-induced perturbations in background light. Preferably, the locating comprises physically aperturing the laser light. Preferably, the fluid flow is provided by an inlet jet orifice and the locating comprises shadowing the inlet jet orifice from the laser light.

In another aspect, the invention provides a method for optically detecting single particles, the method comprising: providing a laser beam in an intracavity laser beam employing a solid state laser medium; directing a flow of particle-containing fluid through the laser beam utilizing an aerosol jet so that light from the laser beam is scattered by the particle; and collecting light scattered by the particle and producing an output signal indicative of the particle, the output signal being essentially free from noise caused by the shedding of turbulent eddies from the interior walls of the aerosol jet. Preferably, the particle has a size of 0.1 micron or less.

In yet another aspect, the invention provides a method for optically detecting single particles in a laser cavity, the method comprising: optically pumping a laser medium within the laser cavity to produce laser light; gain-aperturing the laser cavity; directing a fluid flow containing particles into the laser cavity, the fluid flow including eddy currents; collecting laser light scattered from the particles to produce an output indicative of the single particles; and inhibiting the provided laser light from impinging on the eddy currents. Preferably, the inhibiting comprises physically aperturing the laser light. Preferably, the inhibiting comprises shadowing an inlet jet orifice from illumination by the produced laser light. Preferably, the shadowing comprises locating a first optical stop structure between a source of a the laser light and the inlet jet orifice. Preferably, the shadowing further comprises locating a second optical stop structure between a laser cavity end mirror and the inlet jet orifice. Preferably, the physically aperturing comprises providing a first aperture assembly between the laser medium and the detecting region and a second aperture assembly between a laser cavity end mirror and the detecting region.

In yet another aspect, the invention provides a device for intracavity detection of particles, the device comprising: a laser cavity; a solid-state laser medium disposed within the laser cavity; an optical pump source directed toward the solid-state laser medium; a focusing unit for focusing pumping light provided by the optical pump source into the solid-state laser medium to achieve gain-aperturing of the laser cavity and to excite the solid-state laser medium to provide laser light within the laser cavity; a particle source for introducing particles into a detecting region within the laser cavity and in the path of the laser; a detection optics assembly located to collect light from the detecting region; and an optical barrier complex for shielding eddy current fluid flow, occurring in a region from which light can get into the detecting region, from exposure to the laser light. Preferably, the optical barrier complex comprises a physical aperture. Preferably, the optical barrier complex comprises: a first aperture assembly located between the optical pump source and the detecting region; and a second aperture assembly located between a laser cavity end mirror of the provided laser light and the detecting region. Preferably, the first aperture assembly includes an aperture plate. Preferably, the first aperture assembly includes a plurality of aperture plates. Preferably, the second aperture assembly includes an aperture plate. Preferably, the second aperture assembly includes a plurality of aperture plates. Preferably, the optical barrier complex comprises an optical stop. Preferably, the optical barrier complex comprises: a first optical stop structure located between the optical pump source and the region in which the eddy current fluid flow occurs; and a second optical stop structure located between the laser cavity end mirror of the provided laser light and the region in which the eddy current fluid flow occurs. Preferably, the region in which the eddy current fluid flow occurs is proximate to an inlet jet orifice. Preferably, the solid-state laser medium is a doped medium. Preferably, the optical pump source is a semiconductor laser.

According to yet another aspect, the invention provides an optical particle counter comprising: a gain-apertured laser cavity producing laser light; an inlet jet providing fluid flow into a particle detecting region within the laser cavity, the inlet jet having an inlet jet orifice; a detection optics assembly located to collect light scattered from particles with the detecting region for producing an output signal indicative of the particles; and an optical barrier complex located to reduce noise as compared to the gain-apertured system without the optical barrier complex for fluid flow rates greater than or equal to about 0.1 cubic feet per minute. Preferably, the optical barrier complex comprises an aperture assembly providing physical aperturing of the laser light. Preferably, the optical barrier complex comprises a first optical stop structure for shadowing the inlet jet orifice from exposure to the laser light. Preferably, the first optical stop structure, the gain aperturing, and the physical aperturing cooperate to eliminate flow-induced background light perturbations in the particle counter. Preferably, the aperture assembly consists essentially of a single aperture plate. Preferably, the aperture assembly comprises a plurality of aperture plates. Preferably, the inlet jet orifice is recessed away from the laser light by between 0.010 inches and 0.040 inches with respect to an end of the first optical stop structure. Preferably, the optical barrier complex comprises a first optical stop structure for shadowing the inlet jet orifice from exposure to the laser light. Preferably, the first optical stop structure consists essentially of a single optical stop. Preferably, the first optical stop structure comprises a plurality of optical stops. Preferably, the optical barrier complex further comprises a second optical stop structure on an opposite side of the inlet jet orifice from the first optical stop structure.

The invention permits a gain apertured cavity to be used to reliably detect particles of 0.065$\mu$ (micron) or smaller at a flow rate of 1.0 cubic feet per minute, with a counting efficiency of greater than or equal to 30%. The above and other advantages of the present invention may be better understood from a reading of the following description of the preferred exemplary embodiments of the invention taken in conjunction with the drawings in which:

BRIEF DESCRIPTION OF THE DRAWINGS

FIG. 1 is an exploded perspective view of a particle counter according to one embodiment of the present invention;

FIG. 2 is an exploded perspective view of a light trap assembly;

FIG. 3A is a plane view of an aperture plate;

FIG. 3B is a side view of an edge of the aperture plate shown in FIG. 3A;

FIG. 4 is a schematic side view of a particle counter according to a preferred embodiment of the present invention;

FIG. 5A is a top plane view of an inlet jet nozzle;

FIG. 5B is a side view of the inlet jet nozzle shown in FIG. 5A;

FIG. 5C is a sectional view of the inlet jet nozzle shown in FIG. 5A;

FIG. 5D is a perspective view of the inlet jet nozzle shown in FIG. 5A;

FIG. 6A is a perspective view of a nozzle housing;

FIG. 6B is a top plane view of the nozzle housing depicted in FIG. 6A;

FIG. 6C is a front end view of the nozzle housing depicted in FIG. 6A; and FIG. 7 is a top cross-sectional view of an inlet jet in proximity to a laser beam.

DETAILED DESCRIPTION OF THE PREFERRED EMBODIMENT

In this disclosure, the term "light" is not limited to visible radiation but is used in a broad sense meaning any electromagnetic radiation. In this disclosure, laser light emerging directly from a laser apparatus is "original laser light"; and laser light reflected by a laser cavity end mirror is "reflected laser light".

In this disclosure, an aperture assembly includes one or more physical apertures. An "aperture assembly" is equivalent to "light trap assembly" 105 depicted in FIGS. 1, 2, and 4. In this disclosure "aperture," "physical aperture," and "aperture plates" are equivalent. In this disclosure, an "optical stop structure" is a structure for preventing diffuse laser light from reaching an orifice for fluid flow, located between this orifice and a source of laser light, or between the orifice and a laser cavity end mirror. A single optical stop structure may include one or more optical stops. A plurality of optical stops may be provided in a single optical stop structure by machining the optical stop structure to provide a plurality of obstacles to light exposure. Alternatively, a collection of separate parts may be assembled to form a multiple-stop optical stop structure. Herein, an "optical stop pair" is an optical stop structure having two optical stops. Herein, an "optical barrier complex" comprises one or more obstructions tending to inhibit the diffusion of laser light toward a selected region. An exemplary optical barrier complex may include one or more aperture assemblies, and/or one or more optical stop structures. An optical barrier complex may include one or more apertures (whether or not included in an aperture assembly) and/or one or more optical stops (whether or not included in an optical stop structure). An exemplary optical barrier complex may operate to inhibit diffusion of laser light toward a region outside a particle detection region and/or in proximity to an inlet jet orifice.

Figure 4:
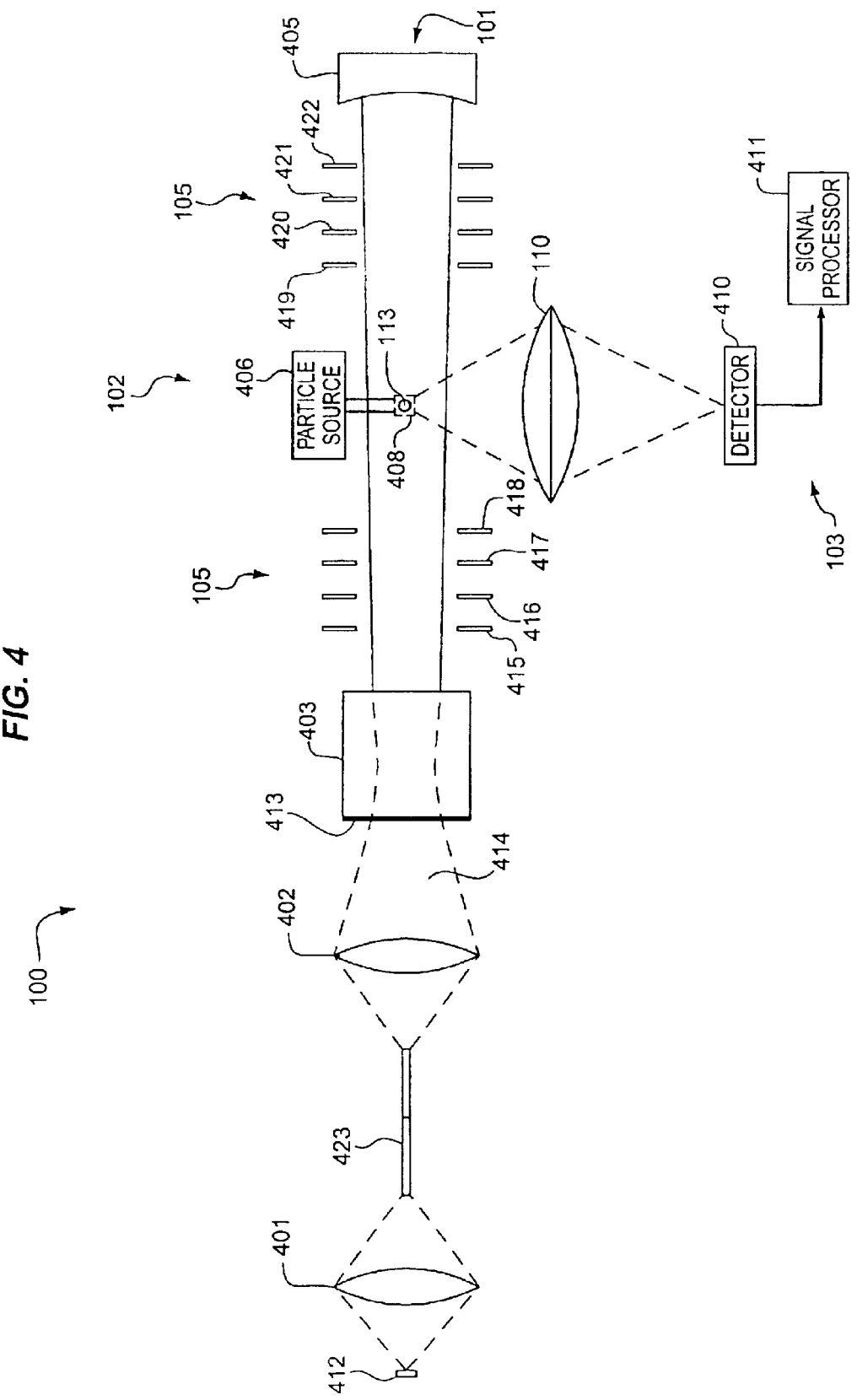

In this disclosure, the terms "laser light", "laser beam", and "laser radiation" are used interchangeably. A "focusing unit" is a device for focusing light including but not limited to a lens for focusing a laser beam, a reflector, and/or a mirror. A "laser cavity end mirror" is located at the opposite end of the laser cavity from the laser crystal (laser medium). Reflector 405 in FIG. 4 illustrates one example of a laser beam reflector mirror. The term "laser beam reflector" is used interchangeably with the term "laser beam reflector mirror". Herein, "optical pumps" and "optical pump sources" are sources of light for irradiating a laser medium.

It is noted that this disclosure is limited to fluid particle counters, which is a term of art. There are particle counters that detect particles in a vacuum. Because there is no fluid present, or rather any fluid present is rarified as compared to normal fluids, problems associated with fluid flow, light scattering from the fluid, and the apparatus used to control the fluid flow are absent and the physics of such particle counters is significantly different than that of fluid particle counters. Further, it should be noted that particle counters as disclosed herein are designed to be able to detect single particles which are unconstrained in a flowing fluid as distinguished from other systems that detect and analyze the particles of the fluid itself, clouds of particles suspended in a fluid, or particles which are constrained in the fluid, such as constrained to flow in a single line past a light beam. Those skilled in the art recognize that it is a much more difficult task to detect and size single particles flowing unconstrained in a fluid; therefore, the art of particle counting involves different technology than these other particle detection and analysis systems.

It is generally accepted that intracavity OPC noise can come from four sources: (1) electronic noise, (2) optical noise from background light, (3) flow-induced laser power noise, and (4) optical noise from molecular scattering. Electronic noise is generally not a limiting factor for most modern OPCs, as the signal processing systems are designed such that their noise levels are less than those arising from optical noise sources. Optical noise from background light can be a performance-limiting factor for OPCs depending on the design of the optical bench, and the proximity of the detecting region to surfaces which can reflect laser radiation. Flow-induced laser power noise is generally a problem only for intracavity OPCs, and classically refers to noise induced in the laser cavity power by the air flowing through the laser beam. Optical noise from molecular scattering establishes the theoretical limit of performance for all OPCs. It is a goal of OPC designers to reduce noise from all other sources, so that noise from molecular scattering is the dominant noise source.

To minimize flow-induced laser power noise, airflow through the laser beam should be laminar. The existence of laminar flow indicates an absence of turbulence. Providing laminar flow generally requires that the inlet jet orifice be very close to the center of the laser beam, such that the orifice is very close to the detecting region, as defined by the detector field of view. Achievement of laminar flow through the laser beam also benefits from precise alignment of the inlet jet orifice with the laser beam.

In the system of the '589 patent, particles from a particle source are introduced into a detecting region (sample volume) by an inlet jet having an orifice. Generally, the amount of optical noise due to background light increases with increasing proximity of the inlet jet orifice to the detecting region. The system of the '589 patent initially appeared to be successful at suppressing optical noise from background light. However, large, transient bursts of noise were later observed which were of unknown origin and which were not controllable. This transient noise prevented the design of the '589 patent from achieving optimal performance characteristics.

The inventors discovered that the observed transient noise generally increased with increasing fluid flow rate and had a low frequency of occurrence, with large bursts occurring only every 0.5 to 5 minutes. Such large noise bursts are problematic, since a single such burst could generate a large number of false particle counts. The inventors initially suspected that flow-induced laser noise was the cause of these large noise bursts. However, a series of observations pertaining to these noise bursts cast doubt on this initial suspicion. Specifically, only a minority of detector elements within a detector array experienced the transient noise bursts. Since different detector elements within the detector array image different portions of the sample volume, it was deduced that the cause of the transient noise was localized within a particular segment of the sample volume. Since noise cancellation signal processing (described in U.S. Pat. No. 4,893,928) assumes flow-induced laser noise to be experienced uniformly over all detector elements in the detector array, the observed large disparity in noise intensity between different detector elements tends to refute the suspicion that flow-induced laser noise was the source of the problem.

Instead, the observed pattern of noise detection among the detector elements is consistent with an event specific to a particular region within or near the sample volume. The inventors observed that the transient nature of the noise was consistent with the generation of turbulent eddy currents from the interior walls of the inlet jet. Accordingly, the volume in proximity to the inlet jet emerged as a "particular region" potentially responsible for the observed transient noise.

The region in proximity to the inlet jet is outside the sample volume of the particle counter but is nevertheless within the range of diffused laser light capable of generating reflections measurable by detector elements. The inventors believed that impingement of diffused laser light on turbulent flow and eddy currents in the inlet jet region could account for the observed transient noise signals. Consequently, the inventor theorized that the observed transient noise resulted from a previously unidentified phenomenon of flow-induced perturbations in background light arising from impingement of diffused laser light on turbulent flow and eddy current fluid flow proximate to the inlet jet orifice.

This theory, which identifies a previously unknown noise source for intracavity DPSSL (Diode Pumped Solid State Laser) OPCs, led to design improvements which allowed achievement of desired design specifications on a predictable basis, and creation of a commercial instrument which is reliable and manufacturable. One improvement introduced in response to suspected cause of the transient noise is the introduction of physical aperturing of the laser beam, in addition to the gain aperturing disclosed in the '589 patent. Another improvement is the machining of optical stops into an inlet jet housing, positioned with respect to the inlet jet so as to consistently achieve adequate shadowing of the inlet jet orifice from exposure to diffused laser light.

FIG. 1 is an exploded perspective view of a particle counter 100 according to one embodiment of the present invention. Particle counter 100 preferably includes laser optics assembly 101, flow chamber assembly 102, and detection optics assembly 103. Laser optics assembly 101 preferably includes laser focusing optics assembly 104, two laser beam aperture assemblies 105 (one on either side of sample block 108), and laser cavity mirror assembly 106. Flow chamber assembly 102 preferably includes inlet jet assembly 107, which includes inlet jet 113, sample block 108, and exhaust port 109. Inlet jet 113 preferably includes inlet jet nozzle 500 and nozzle housing 600 and is discussed in greater detail in connection with FIG. 7. Exhaust bore 115 is shown at the lower right of sample block 108. Detection optics assembly 103 preferably includes two low f-number detector collection optics 110, two photodetector mounts 111, and two photodetector signal processing assemblies 112. Preferably, programmable equipment in communication with signal processing assemblies 112, including equipment for particle counting and sizing, is handled by a main processor board (not shown). In one embodiment, one of each of items 110–112 is located on each side of sample block 108. However, particle counter 100 may be used with just a single set of detection components 110–112.

Figure 2:
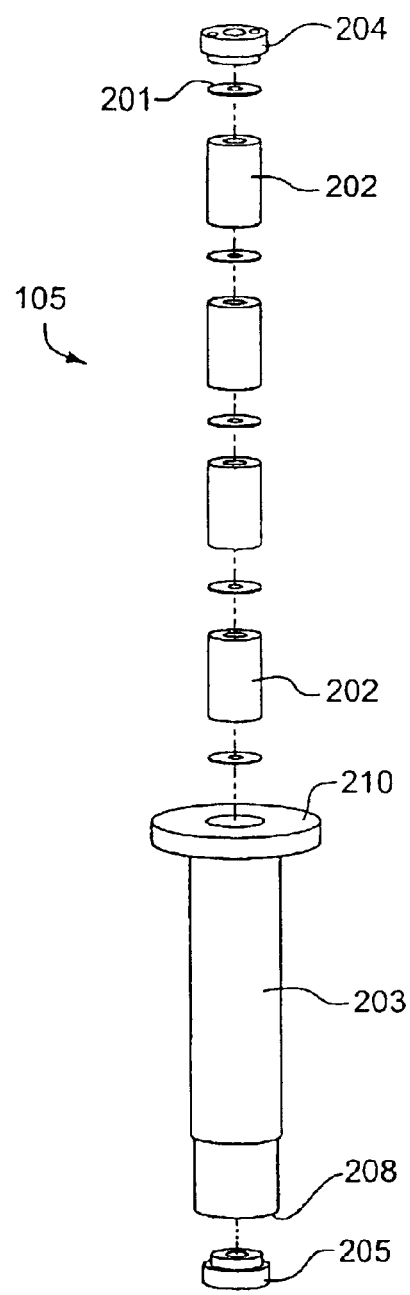

FIG. 2 is an exploded perspective view of light trap assembly 105. Light trap assembly 105 preferably includes light trap housing 203 and end cap 205 attachable to a first end 208 of light trap housing 203. Light trap assembly 105 preferably further includes a plurality of aperture plates 201 separated from one another by light trap spacers 202. Light trap assembly 105 preferably, further includes an end cap 204 attachable to a second end 210 of light trap housing 203. In the embodiment of FIG. 2, there are a total of five aperture plates 201 and a total of four light trap spacers 202. However, any number of aperture plates or "apertures" 201 could be included in light trap assembly 105 along with a suitable number of light trap spacers 202. Preferably, light trap spacers 202 are threaded on the inside and painted black.

Figure 3A:
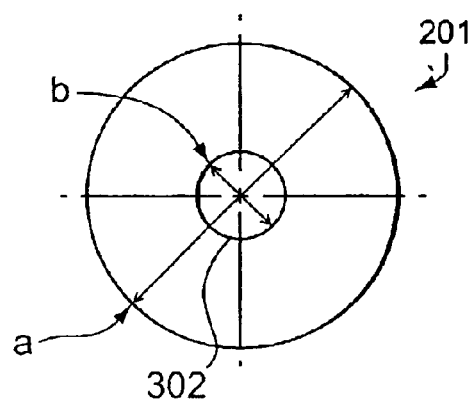
Figure 3B:
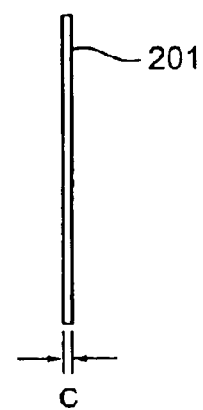

FIG. 3A is a plane view of aperture plate 201, and FIG. 3B is a side view of an edge of aperture plate 201. In one embodiment, outer diameter "a" of aperture plate 201 equals 0.248 inches with a tolerance of +0.000/−0.002 inches, although aperture plates having other diameters may be used. Aperture hole 302 preferably has a diameter "b" of 0.071 inches with a tolerance of +0.003/−0.003 inches, although aperture holes with diameters both smaller and larger than 0.071 inches may be employed. Aperture plate 201 preferably has a thickness "c" of 0.005 inches, although other thicknesses may be used. Aperture plate 201 is preferably made of black anodized aluminum, though other suitable metals, plastics, or other materials may be used.

FIG. 4 is a schematic side view of a particle counter 100 according to a preferred embodiment of the present invention. As discussed in connection with FIG. 1, particle counter 100 preferably includes laser optics assembly 101, flow chamber assembly 102, and detection optics assembly 103. Some of the specific components shown in FIG. 1 are omitted from FIG. 4 for the sake of convenience. However, the three basic component assemblies 101–103 are all shown.

Laser optics assembly 101 preferably includes optical pump source 412, which pump source is preferably a laser diode, first lens assembly 401, fiber optic link 423, second lens assembly 402, coating forming mirror 413, solid state laser medium 403, laser aperture assemblies 105, and second mirror (laser beam reflector mirror) 405. Flow chamber assembly 102 preferably includes particle source 406, detecting region 408, inlet jet 113, and collection optics 110 (also shown in FIG. 1). Detection optics assembly 103 preferably includes detector 410 and signal processor 411. Only a portion of aperture assemblies 105, discussed in connection with FIG. 1, is shown in FIG. 4. Depiction of selected components including the spacers and housing of aperture assemblies 105 are omitted for the sake of simplicity.

Each aperture assembly 105 may include one or more aperture plates. In the embodiment shown in FIG. 4, each aperture assembly 105 includes four apertures plates. Experimental data indicates that desirable performance characteristics are obtained when deploying four aperture plates between laser medium 403 and detecting region 408 and one aperture plate between second mirror 405 and detecting region 408.

Figure 5A:
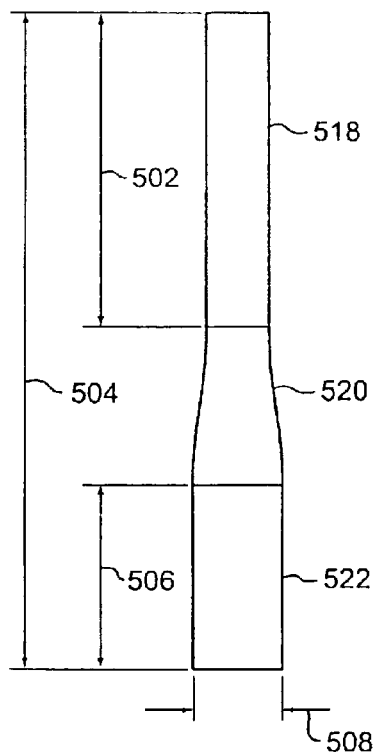
Figure 7:
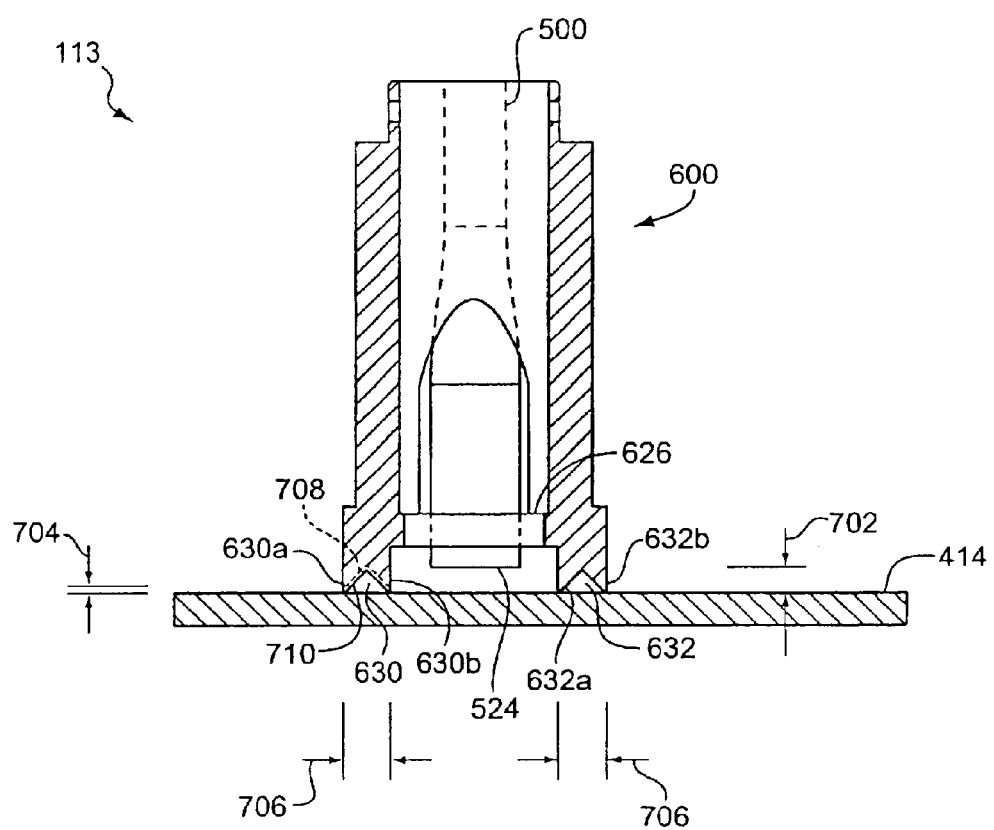

FIG. 5A is a top plane view of an inlet jet nozzle 500, which is a part of inlet jet 113, as shown in FIG. 7. Inlet jet nozzle 500 is preferably made of brass. Inlet jet nozzle outlet 500 preferably includes three basic portions along its length: inlet tube 518 which preferably has a circular cross-sectional geometry, transition region 520, and outlet tube 522, which preferably has a rectangular cross-sectional geometry. As shown in FIG. 5D, inlet jet orifice 524 is located at the open end of outlet tube 522. Inlet jet orifice 524 preferably has a substantially rectangular cross-sectional geometry with rounded portions at opposite ends of the longer portion of this rectangle. This substantially rectangular cross-sectional geometry of orifice 524 preferably has an internal length of 0.394 inches and an internal width of 0.025 inches. However, other internal dimensions for orifice 524 may be employed.

In one embodiment, inlet tube 518 is preferably about 1.49 inches long 502, outlet tube 522 is preferably 0.875 inches +/−0.030 inches long 506, and inlet jet nozzle 500 as a whole is preferably 3.11 inches +/−0.030 inches long. The outside dimension 508 of the width of the outlet tube 522 is preferably 0.412 inches.

Figure 5B:
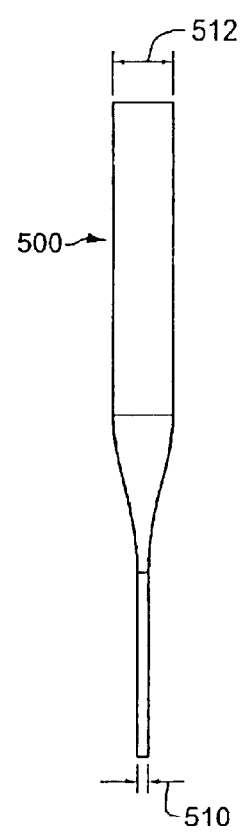
Figure 5C:
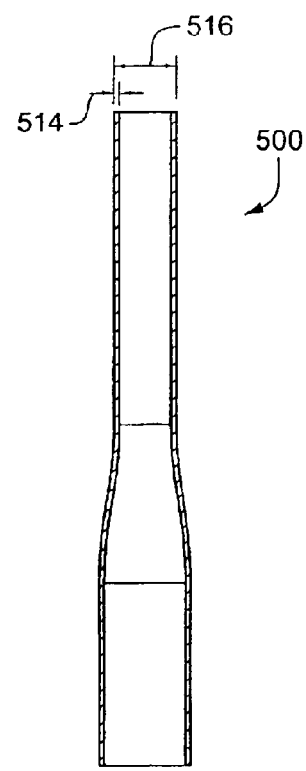
Figure 5D:
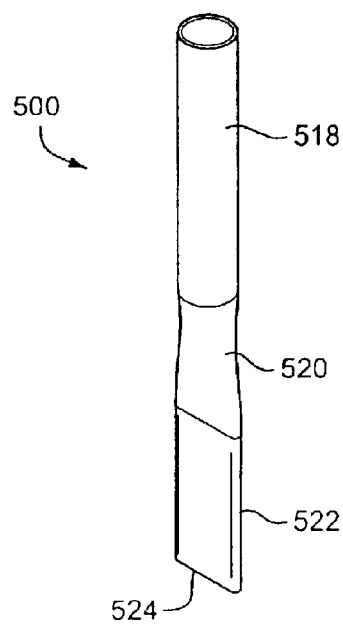

FIG. 5B is a side view of inlet jet nozzle 500 shown in FIG. 5A; FIG. 5C is a sectional view of inlet jet nozzle 500 shown in FIG. 5A; and FIG. 5D is a perspective view of inlet jet nozzle 500 shown in FIG. 5A. The outside diameter 512 of inlet tube 518 is preferably 0.281 inches, although other diameters may be employed. Thickness 514 of the material forming inlet tube 518 is preferably 0.016 inches, leading to an inside diameter 516 of 0.249 inches for inlet tube 516. In one embodiment, outlet tube 522 has an external thickness 510 of 0.057 inches, although other dimensions may be employed.

FIG. 6A is a perspective view of a nozzle housing 600. Nozzle housing 600 is preferably made of a single piece of 6061-T6 Aluminum. However, nozzle housing 600 may be made of other metals or non-metallic materials. Nozzle housing 600 is preferably dimensioned to allow inlet jet nozzle 500 to fit inside nozzle housing 600. Preferably, the combination of inlet jet nozzle 500 and nozzle housing 600 form inlet jet 113.

Nozzle housing 600 generally includes three main components along its length: housing inlet 607, main shaft 603, and optical stop platform 605. Shoulder 601 is the point at which the diameter of nozzle housing 600 expands from that of housing inlet 607 to that of main shaft 603. The optical stops forming part of optical stop platform 605 are discussed in connection with FIGS. 6B and 6C.

FIG. 6B is a top plane view of nozzle housing 600 depicted in FIG. 6A. In addition to the elements of nozzle housing 600 discussed in connection with FIG. 6A, optical stops 630-a, 630-b, 632-a, and 632-b are shown. Orifice sleeve 626 is also shown. Orifice sleeve 626 is preferably dimensioned to allow outlet tube 522 of inlet jet nozzle 500 to pass therethrough. Orifice sleeve 626 is preferably a substantially rectangular cross-section hole through a portion of optical stop platform 605.

Main shaft 603 is preferably 0.690 inches wide 602. Distance 610 from inlet end 609 of nozzle housing 600 to the inner edge of orifice sleeve 626 is preferably 1.28 inches. Distance 612 from inlet end 609 of nozzle housing 600 to the outer edge of orifice sleeve 626 is preferably 1.388 inches. The stated dimensions establish a preferred length of orifice sleeve 626. It will, however, be appreciated that different lengths of orifice sleeve 626 may be deployed in nozzle housing 600. Optical stop platform 605 is preferably 0.772 inches wide.

In a preferred embodiment, optical stop structures 630 and 632 have substantially the same lengths and are symmetrically located with respect to inlet jet orifice 524 once inlet jet nozzle 500 (not shown in FIG. 6B) is properly positioned within nozzle housing 600. In this preferred embodiment, the distances 604, 614 between the farthest extent of optical stops 630-a, 630-b, 632-a, and 632-b and inlet end 609 of nozzle housing 600 is 1.510 inches. Preferably, optical stops 630-a, 630-b, 632-a, and 632-b all extend 0.014 inches beyond inlet jet orifice 524 (not shown).

In an alternative embodiment, there is an asymmetry between distances 604 and 614 from the ends of optical stop structures 630 and 632, respectively, to inlet end 609 of nozzle housing 600. Specifically, distance 614 from inlet end 609 of nozzle housing 600 to the end of optical stop structure 632 is preferably 1.1510 inches. In this alternative embodiment, distance 604 from inlet end 609 of nozzle housing 600 to the farthest extent of optical stop structure 630 is preferably 1.502 inches. The described geometry is established under the assumption that original laser light travels from right to left, in the view of FIG. 6B.

Accordingly, reflected laser light travels from left to right in the view of FIG. 6B. Experimentation has shown that reflected laser light can be effectively shadowed with less intrusion of optical stops into the path of a laser beam.

FIG. 6C is a front-end view of nozzle housing 600 depicted in FIG. 6A. The preferably rectangular outline of optical stop platform 605 is shown surrounding orifice sleeve 626. Behind optical stop platform 605, in the view of FIG. 6C, is a shoulder 601 of main shaft 603 and housing inlet 607.

In one embodiment, orifice sleeve 626 is a passage through optical platform 605 having a substantially rectangular cross-section with rounded edges at the ends of the long dimension of the rectangle. Rounded ends 620 of orifice sleeve 626 are preferably machined as half-circles with a consistent radius of curvature, although other geometries may be employed. Orifice sleeve 626 is preferably dimensioned to closely match the external dimensions of outlet tube 522. Once inlet jet 113 is assembled, outlet 522 of inlet jet nozzle 500 preferably fits snugly through orifice sleeve 626.

In one embodiment, orifice sleeve 626 has a length 616 of 0.424 inches +0.005/−0.000 inches. Preferably, orifice sleeve 626 has a width of 0.062 inches +0.005/−0.000 inches. It is noted that this width is expected to receive nozzle outlet 522 having an external thickness of 0.057 inches (FIG. 5B), providing about 0.015 inches of clearance. In an alternative embodiment, inlet jet nozzle 500 may be replaced by a nozzle made by electron discharge machining to provide a smooth transition region from a circular cross-section inlet tube to a substantially rectangular cross-section outlet tube.

FIG. 7 is a top cross-sectional view of inlet jet 113 in proximity to laser beam 414. In the embodiment shown in FIG. 7, inlet jet 113 includes inlet jet nozzle 500 and nozzle housing 600. For the sake of simplicity, some geometric detail of inlet jet nozzle 500 and nozzle housing 600 discussed in connection with other figures herein have been omitted from the discussion of FIG. 7. For the sake of the instant discussion, the ends of optical stops 632-a and 632-b are considered to be right at the edge of laser beam 414. In the embodiment of FIG. 7, optical pump source 412 (not shown) is to the right of inlet jet 113, and laser beam reflector mirror 405 (not shown) is to the left of inlet jet 113.

In the embodiment of FIG. 7, inlet jet nozzle 500 is located inside nozzle housing 600 such that inlet jet orifice 524 is recessed a selected distance 702 from optical stops 632-a and 632-b. Experimental results indicate that shadowing of inlet jet orifice 524 from laser beam 414 is optimum when orifice recess distance 702, i.e., the distance between inlet jet orifice 534 and the distal end of the optical stops, is between 0.010 inches and 0.040 inches. However, orifice recess distance 702 is adjustable, and other recess distances may be selected. The recess distance 702 is preferably symmetrical. That is, it the same whether measured from stop pair 630 or stop pair 632. However, it may also be asymmetrical, that is the distance measured with respect to stop pair 630 may be different than the distance measured with respect to stop pair 632. One preferred diameter for laser beam 414 is about 0.0315 inches (0.8 millimeters [mm]). In one embodiment of particle counter 100, inlet jet orifice 524 is preferably located between 0.03075 inches to 0.059 inches, and more preferably between 0.043 inches and 0.059 inches, from the center of laser beam 414. In one embodiment, the individual optical stops within optical stop pairs 630 and 632 have a separation distance 706 of 0.140 inches +/−0.002 inches.

Two possible lengths are shown for optical stop pair 630 in FIG. 7. Consistent with the preferred symmetrical embodiment, discussed above, length 710 shows optical stop pair 630 extending as far toward beam 414 as optical stop pair 632. And, consistent with an alternative asymmetrical embodiment, discussed above, length 708 shows optical stop pair 630 recessed by optical stop recess mismatch distance 704 with respect to optical stop pair 632. Typically, optical stop mismatch distance 704 equals 0.008 inches +/−0.002 inches.

In one embodiment, optical stops 630-a, 630-b, 632-a, and 632-b are coated with Cardinal® Velvethane optical black paint to optimize shadowing of inlet jet orifice 524. This paint is preferably a two-component high solids polyurethane paint and is available from Cardinal Industrial Finishes, 1329 Potrero Ave., South El Monte, Calif. 91733.

In FIG. 7, a total of four optical stops 630-a, 630-b, 632-a, and 632-b are shown; however, it will be appreciated that fewer or more than four optical stops may be employed to shadow the inlet jet orifice from undesired exposure to laser radiation. In general, it is desirable to employ one or more optical stops on each side of inlet jet orifice 524, to protect inlet jet orifice 524 from both original laser light and reflected laser light. Experimentation has shown that beneficial results are obtained when employing two optical stops on each side of inlet jet orifice 524. Accordingly, in the embodiment of FIG. 7, two optical stops are deployed on each side of inlet jet orifice 524. The deployment of the number and location of optical stops 630, 632 as shown in FIG. 7 combines effective shadowing of inlet jet orifice 524 with a reasonably small space requirement for the optical stops.

While a total of four optical stops 630-a, 630-b, 632-a, and 632-b are depicted in FIG. 7, any number of optical stops may be employed. Specifically, inlet jet orifice 113 may operate with only a single optical stop or with one optical stop on either side of inlet jet orifice 524. The use of only a single optical stop to the right (in the view of FIG. 7) of inlet jet orifice 524 would provide less shadowing of inlet jet orifice 524 than would the embodiment depicted in FIG. 7. However, the deployment of only a single optical stop on one side of inlet jet orifice 524 advantageously occupies less space than the embodiment depicted in FIG. 7. Accordingly, where space requirements are at a premium, a single-optical stop embodiment could be beneficially employed. In another alternative embodiment, three or more optical stops could be employed on one or more sides of inlet jet orifice 524.

Referring to FIGS. 1–7, particle counter 100 preferably operates as described below. In a preferred embodiment, particle counter 100 disclosed in this application differs from that disclosed in the '589 patent through the inclusion of aperture assemblies 105 and optical stops 630 and 632. Accordingly, the following discussion is directed primarily to the operation of the aperture assemblies and the optical stops. The reader is directed to the '589 patent for a discussion of those features common to the '589 patent and the instant disclosure.

Preferably, optical pump source 412 creates laser beam 414 which passes through first lens assembly 401, fiber optic link 423, second lens assembly 402, coating forming mirror 413, solid state laser medium 403, laser aperture assemblies 105, and laser beam reflector mirror 405. A first aperture plate 415 (which corresponds to aperture plate 201 shown in FIG. 2) within aperture assembly 105 preferably masks laser beam 414 to remove most of the noise, but creates an undesirable diffraction pattern in so doing. A second aperture plate 416, within aperture assembly 105, absorbs the diffraction pattern created by first aperture plate 415, but in turn generates its own diffraction pattern, which is significantly less intense than the diffraction pattern from first aperture plate 415. Continuing this pattern, each succeeding aperture plate preferably masks the diffraction from a previous aperture plate and produces a reduced diffraction pattern of its own. In this manner, successions of aperture plates (such as aperture plates 415–418 and aperture plates 419–422) disposed in the path of laser beam 414 preferably produce a progressively smaller diffraction pattern with each succeeding aperture plate. In the embodiment of FIG. 4, laser aperture assemblies 105 preferably aid in shadowing inlet jet orifice 524, thereby reducing flow-induced noise in the background light. Aperture assemblies 105 preferably combine with the gain-aperturing discussed in the '589 patent to provide high power operation in a low noise environment.

A source of fluid, which is preferably a gas in particle counter 100, and typically air, is provided by particle source 406. The fluid is directed through inlet jet 113 toward detecting region 408. While in detecting region 408, the fluid passes through laser beam 414, thereby generating scattering of the laser light from particles within the fluid. Scattering from particles in detecting region 408 are preferably directed to focusing lens 409 and toward detector 410. Signals indicative of the reflections are then preferably sent from detector 410 to signal processor 411.

Attention is directed to FIG. 7 in connection with the operation of optical stops 630-a, 630-b, 632-a, and 632-b. In the embodiment of FIG. 7, optical stop structures 630 and 632 each have two optical stops and are, therefore, optical stop pairs according to the previously provided definitions. Generally, laser beam 414 is generated from optical pump 412 at the right (FIG. 4), and reflected by laser beam reflector mirror 405 on the left hand side. Accordingly, original laser light approaches inlet jet 113 from the right, and reflected laser light approaches inlet jet 113 from the left. Original laser light encounters optical stop structure 632 upon approaching inlet jet 113 and is thus inhibited from reaching inlet jet orifice 524. Preferably, optical stop structure 632 extends to a point adjacent to laser beam 414. Recess distance 702 of inlet jet orifice 524 with respect to optical stop structure 632 preferably causes inlet jet orifice 524 to be shadowed from exposure to original laser light within laser beam 414.

Generally, providing a plurality of optical stops within an optical stop structure reduces noise more effectively than using a single optical stop. Generally, each optical stop reduces the amount of noise present in diffused laser light striking the stop. Generally, two optical stops in succession are sufficient to reduce the optical noise to an acceptable level. For this reason, and because of space considerations, the embodiment shown in FIG. 7 includes two optical stops in each of optical stop structures 630 and 632. However, any number of optical stops may be included within each optical stop structure.

A performance-limiting measure of noise in existing particle counting systems arises from the impingement of diffused laser light (or stray light) upon eddy currents outside a detecting region, in the vicinity of an inlet jet. The technology disclosed herein addresses this problem by employing apertures 415–422 which generally reduce the width of the laser beam 414 and the intrusion of laser beam 414 and diffused laser light therefrom into the vicinity of inlet jet orifice 524. This reduced intrusiveness preferably reduces the problematic impingement of laser light upon eddy currents proximate to inlet jet orifice 524. Optical stop structures 630 and 632 preferably operate to still further reduce this problematic impingement of laser light on eddy currents by shadowing the volume including inlet jet orifice 524 from exposure to diffused light from laser beam 414. The combination of apertures 415–422 and optical stop structures 630 and 632 preferably combine to reduce noise arising from laser light impingement on eddy currents sufficiently to allow molecular scattering noise to be the dominant noise source within particle counter 100.

There has been described a novel laser particle counter. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. It is also evident that the methods recited may, in many instances, be performed in a different order; or equivalent structures and processes may be substituted for the various structures and processes described. Consequently, the invention is to be construed as embracing each and every novel feature and novel combination of features present in and/or possessed by the invention herein described.

We claim:

1. A method for intracavity laser detection of optically detecting single particles, said method composing:

providing a solid state laser cavity having laser light;

gain-aperturing said laser cavity with an optical pump;

providing fluid flow including a particle at a detection region within said gain-apertured laser cavity illuminated by said laser light;

collecting light scattered by said particle and producing an output signal indicative of said particle; and locating an optical barrier complex to reduce noise in said output signal at flow rates of said fluid flow greater than or equal to 0.1 cubic feet per minute.

2. The method of claim 1 wherein said particle has a size of 0.1 micron or less.

3. The method of claim 1 wherein said locating comprises locating said optical barrier complex to reduce flow-induced perturbations in background light.

4. The method of claim 1 wherein said locating comprises physically aperturing said laser light.

5. The method of claim 1 wherein said fluid flow is provided by an inlet jet orifice and said locating comprises shadowing said inlet jet orifice from said laser light.

6. A method for optically detecting single particles in a laser cavity, said method comprising:

optically pumping a laser medium within said laser cavity to produce laser light;

gain-aperturing said laser cavity;

directing a fluid flow containing particles into said laser cavity, said fluid flow including eddy currents;

collecting laser light scattered from said particles to produce an output indicative of said single particles; and inhibiting said provided laser light from impinging on said eddy currents by providing a first aperture assembly between said laser medium and said detecting region and a second aperture assembly between a laser cavity end mirror and said detecting region.

7. A method for optically detecting single particles in a laser cavity, said method comprising:

optically pumping a laser medium within said laser cavity to produce laser light;

gain-aperturing said laser cavity;

directing a fluid flow containing particles into said laser cavity through an inlet jet orifice, said fluid flow including eddy currents;

collecting laser light scattered from said particles to produce an output indicative of said single particles; and inhibiting said provided laser light from impinging on said eddy currents by locating a first optical stop structure between a source of a said laser light said inlet jet orifice and locating a second optical stop structure between a laser cavity end mirror and said inlet jet orifice.

8. A device for intracavity detection of particles, said device comprising:

a laser cavity;

a solid-state laser medium disposed within said laser cavity;

an optical pump source directed toward said solid-state laser medium;

a focusing unit for focusing pumping light provided by said optical pump source into said solid-state laser medium to achieve gain-aperturing of said laser cavity and to excite said solid-state laser medium to provide laser light within said laser cavity;

a particle source for introducing particles into a detecting region within said laser cavity and in the path of said laser;

a detection optics assembly located to collect light from said detecting region; and an optical barrier complex for shielding eddy current fluid flow, occurring in a region from which light can get into said detecting region, from exposure to said laser light, said optical barrier complex comprising;

a first aperture assembly located between said optical pump source and said detecting region; and a second aperture assembly located between a laser cavity end mirror of said provided laser light and said detecting region.

9. The device of claim 8 wherein said first aperture assembly includes an aperture plate.

10. The device of claim 8 wherein said first aperture assembly includes a plurality of aperture plates.

11. The device of claim 8 wherein said second aperture assembly includes an aperture plate.

12. The device of claim 8 wherein said second aperture assembly includes a plurality of aperture plates.

13. The device of claim 8 wherein said optical barrier complex comprises an optical stop.

14. The device of claim 8 wherein said optical barrier complex comprises:

a first optical stop structure located between said optical pump source and said region in which said eddy current fluid flow occurs; and a second optical stop structure located between said laser cavity end mirror of said provided laser light and said region in which said eddy current fluid occurs.

15. The device of claim 8 wherein said region in which said eddy current fluid flow occurs is proximate to an inlet jet orifice.

16. The device of claim 8 wherein said solid-state laser medium is a doped medium.

17. The device of claim 8 wherein said optical pump source is a semiconductor laser.

18. An optical particle counter comprising:
    a gain-apertured laser cavity producing laser light;
    an inlet jet providing fluid flow into a particle detecting region within said laser cavity, said inlet jet having an inlet jet orifice;
    a detection optics assembly located to collect light scattered from particles with said detecting region for producing an output signal indicative of said particles; and
    an optical barrier complex located to reduce noise as compared to said gain-apertured system without said optical barrier complex for fluid flow rates greater or equal to 0.1 cubic feet per minute.

19. The particle counter of claim 18 wherein said optical barrier complex comprises an aperture assembly providing physical aperturing of said laser light.

20. The particle counter of claim 19 wherein said optical barrier complex comprises a first optical stop structure for shadowing said inlet jet orifice from exposure to said laser light.

21. The particle counter of claim 20 wherein said first optical stop structure, said gain aperturing, and said physical aperturing cooperate to eliminate flow-induced background light perturbations in said particle counter.

22. The particle counter of claim 19 wherein said aperture assembly consists essentially of a single aperture plate.

23. The particle counter of claim 19 wherein said aperture assembly comprises a plurality of aperture plates.

24. The particle counter of claim 19 wherein said inlet jet orifice is recessed away from said laser light by between 0.010 inches and 0.040 inches with respect to an end of said first optical stop structure.

25. The particle counter of claim 18 wherein said optical barrier complex comprises a first optical stop structure for shadowing said inlet jet orifice from exposure to said laser light.

26. The particle counter of claim 25 wherein said first optical stop structure consists essentially of a single optical stop.

27. The particle counter of claim 25 wherein said first optical stop structure comprises a plurality of optical stops.

28. The particle counter of claim 25 wherein said optical barrier complex further comprises a second optical stop structure on an opposite side of said inlet Jet orifice from said first optical stop structure.

* * * * *